United States Patent [19]

Williams et al.

[11] 4,105,021
[45] Aug. 8, 1978

[54] METHOD AND ARRANGEMENT FOR MEASURING BLOOD PRESSURE

[75] Inventors: William J. Williams; William J. Heetderks, both of Ann Arbor, Mich.

[73] Assignees: Joseph H. Allen; Leonard S. Weisman, both of Madison Heights, Mich.

[21] Appl. No.: 714,097

[22] Filed: Aug. 13, 1976

[51] Int. Cl.² .............................................. A61B 5/02
[52] U.S. Cl. ............................ 128/2.05 A; 128/2.05 P
[58] Field of Search .................... 128/2.05 A, 2.05 C, 128/2.05 E, 2.05 P, 2.05 M

[56] References Cited
U.S. PATENT DOCUMENTS

| | | | |
|---|---|---|---|
| 2,352,875 | 7/1941 | Williams et al. | 128/2.05 A |
| 3,229,685 | 4/1963 | Ringkamp et al. | 128/2.05 A |
| 3,482,565 | 12/1969 | Gowen | 128/2.05 A |
| 3,675,640 | 7/1972 | Gatts | 128/2.06 R |
| 3,841,314 | 10/1974 | Page | 128/2.05 A |
| 3,903,872 | 9/1975 | Link | 128/2.05 A |
| 3,996,926 | 12/1976 | Birnbaum | 128/2.05 A |
| 4,009,709 | 3/1977 | Link et al. | 128/2.05 A |

Primary Examiner—Robert W. Michell
Assistant Examiner—Francis J. Jaworski
Attorney, Agent, or Firm—Krass & Young

[57] ABSTRACT

A method and arrangement for the indirect measurement of systolic and diastolic blood pressure is disclosed which involves applying an occluding inflatable cuff to a body member, with the pressure applied thereby being cycled between a pressure greater than systolic and a pressure less than diastolic. Systolic blood pressure is detected by sensing the point in the pressure cycle at which the blood flow in the occluded member shifts between a flow and no flow condition, while diastolic blood pressure is detected by sensing a characteristic change in slope of blood pulse wave form changes occurring with changing cuff pressures which occurs at a cuff pressure equal to the diastolic pressure. An approach for correcting the systolic and diastolic pressure measurements obtained by this method at one point of the body to give equivalent readings of the systolic and diastolic blood pressure at another point is also disclosed.

18 Claims, 6 Drawing Figures

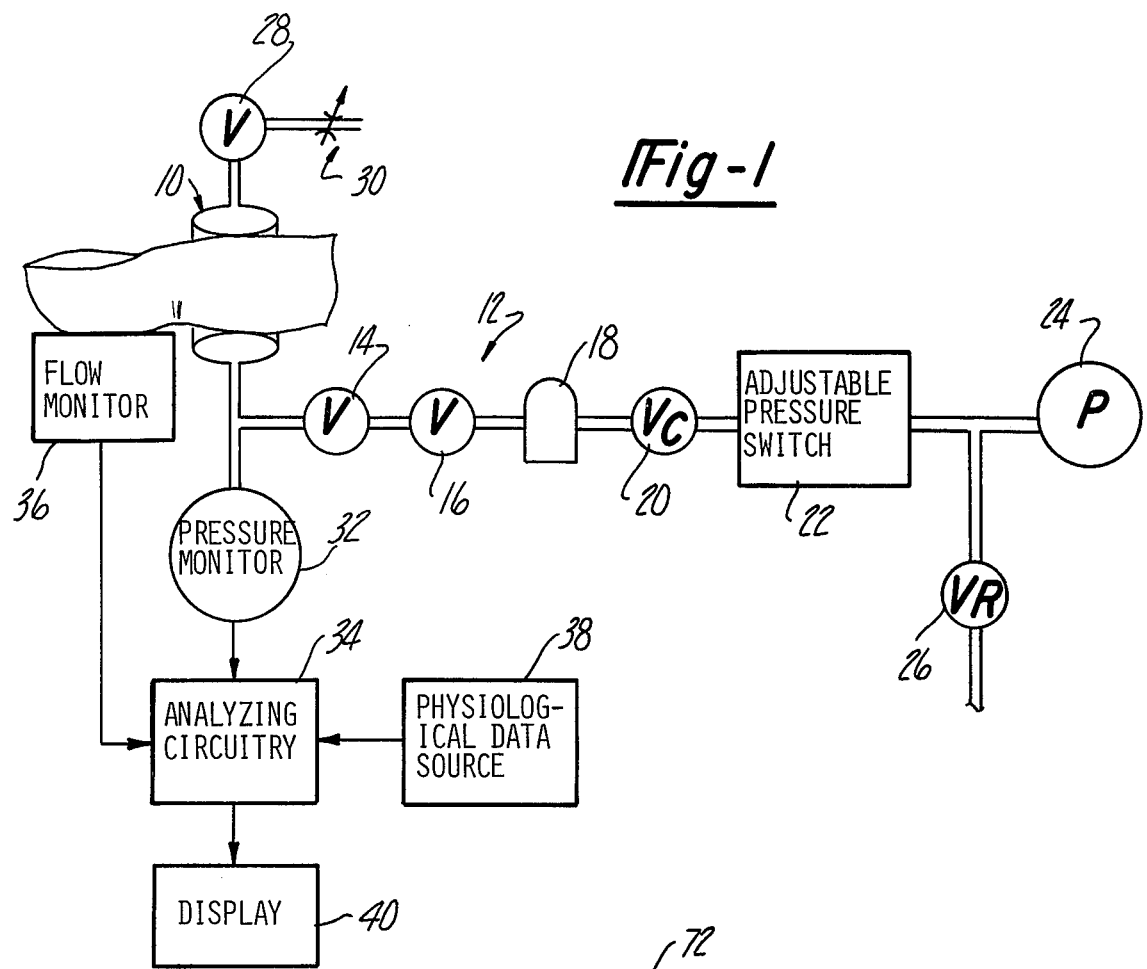
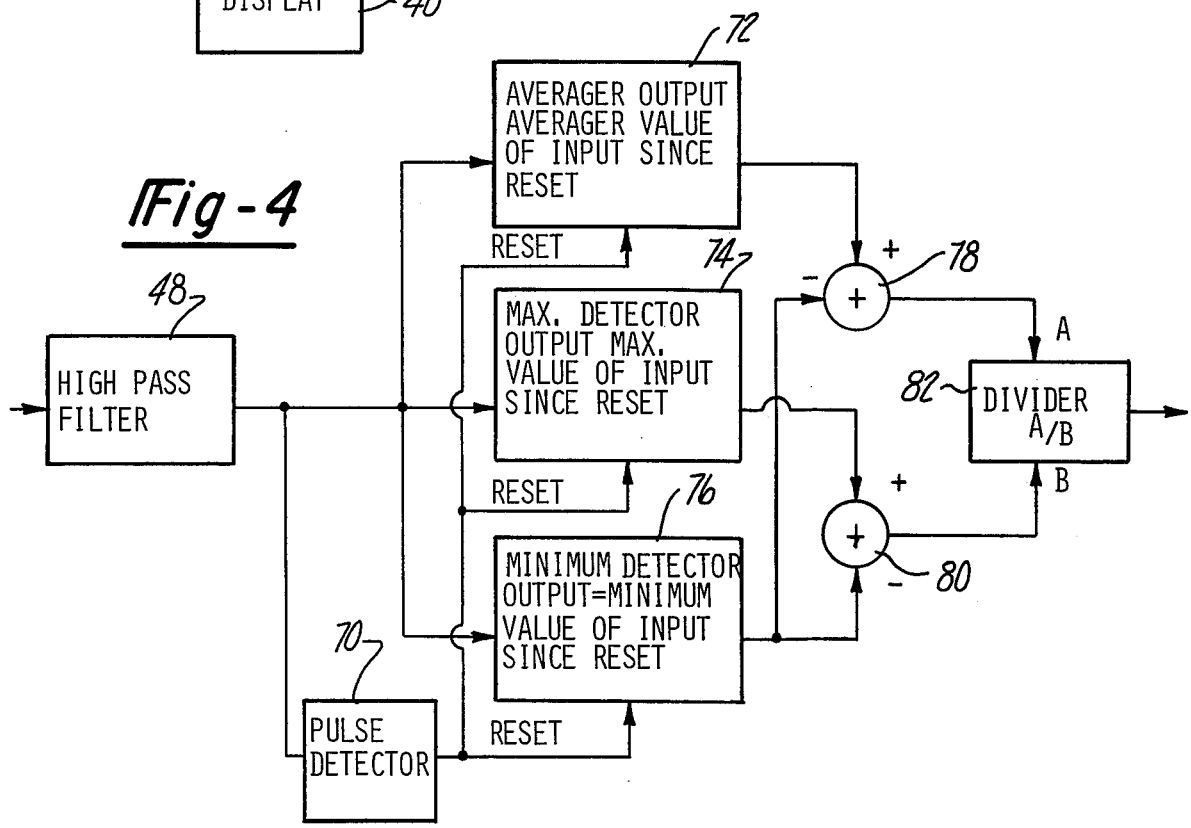

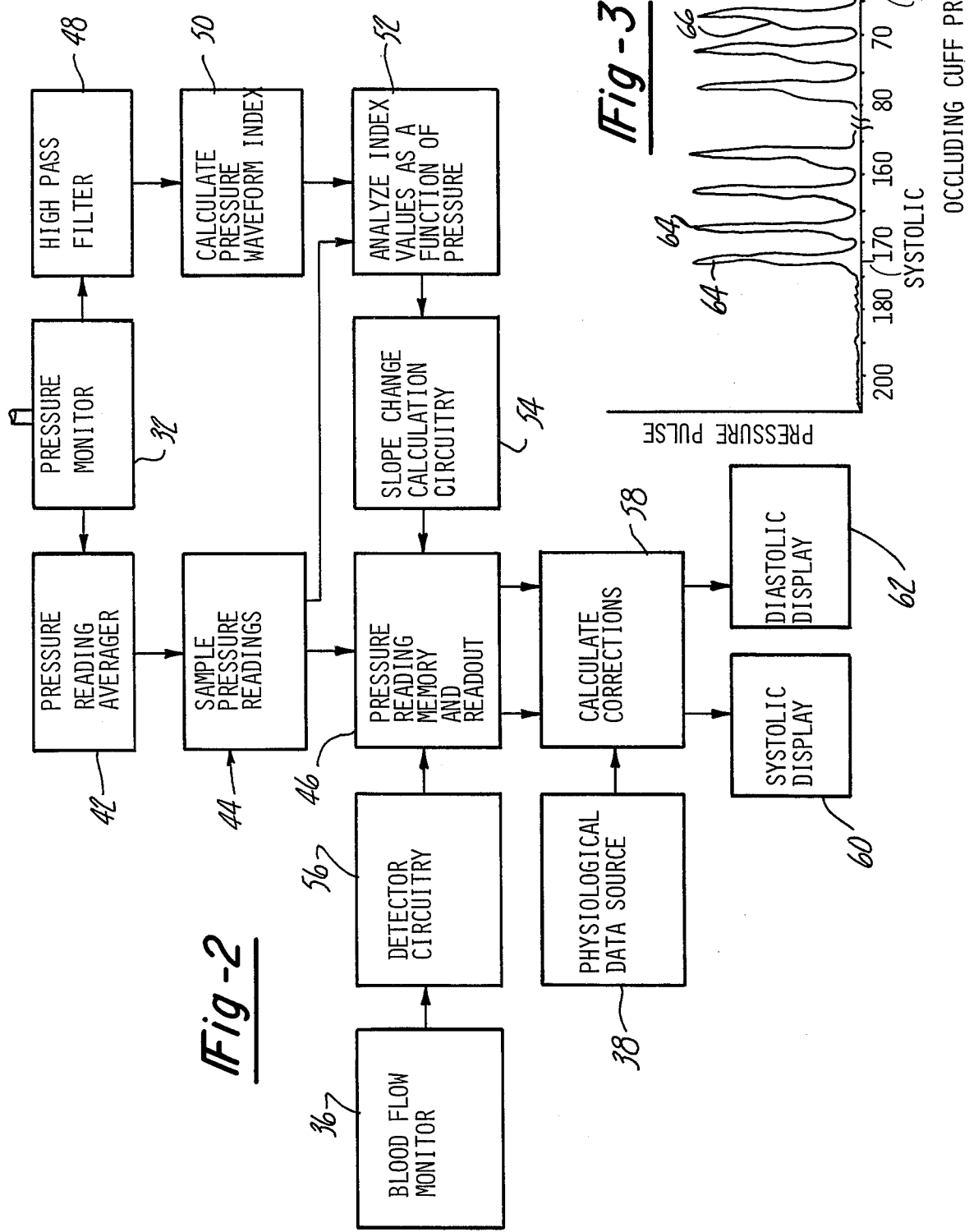

METHOD AND ARRANGEMENT FOR MEASURING BLOOD PRESSURE

BACKGROUND OF THE INVENTION

1. Field of the Invention

This invention is concerned with blood pressure measurement in which a determination of the systolic and diastolic blood pressure may be obtained by a method which is adaptable to automated apparatus.

2. Description of the Prior Art

The measurement of systolic and diastolic blood pressure commonly is carried out by a physician or nurse by the use of an inflatable cuff placed on the upper arm of the subject which is inflated to a pressure higher than the systolic blood pressure, causing an occlusion of the arterial vessels in the upper arm. The pressure in the cuff is then allowed to decline to a point less than the diastolic blood pressure which allows the unoccluded blood flow to resume. By use of a stethoscope the physician or nurse listening to the characteristic sounds (referred to as the "Korotkoff sounds") which have a characteristic transition associated with the systolic and diastolic pressures, the clinician may determine the cuff pressures at systolic and diastolic.

Due to the extremely widespread nature of the hypertensive condition, mass screening of the population for abnormal blood pressures has been recognized as a desirable objective, which mass screening would almost necessarily be carried out without the need for skilled physicians or nurses, i.e. the process would have to be automated. Numerous techniques for such automation have been proposed and implemented. Many of these involve the automated processing of data corresponding to the Korotkoff sounds in order to detect the systolic and diastolic pressures without the need for a skilled observer. These automated techniques relying on such Korotkoff sounds have certain disadvantages, one of which is the impracticality of its use in a relatively noisy environment.

This sensitivity to environmental noise usually has required the cuff to be placed about the upper arm of the subjects since these sounds are much attenuated and would not occur at a lower limb situs such as the wrist or finger. This placement on the upper arm requires partial disrobing of the subject and also is a relatively cumbersome procedure.

Other approaches to this objective have yielded techniques which can reliably detect systolic pressure, but in the case of detecting the diastolic pressure level, these techniques have produced rather poor results.

It is therefore the objective of the present invention to provide a method and arrangement for noninvasively determining the systolic and diastolic blood pressure which is readily adaptable to be automated while producing reliable results. It is another object of the present invention to provide such a technique which does not require the application of cuffs or other devices to the upper arm, but may be applied to the outer extremities, such as the index finger or wrist.

SUMMARY OF THE INVENTION

These and other objects which will become apparent upon reading the following specifications and claims are accomplished by applying an occluding inflatable cuff to a body member, with the pressure applied thereby being cycled between a pressure greater than systolic and a pressure less than diastolic. Systolic blood pressure is detected by sensing the point in the pressure cycle at which the blood flow in the occluded member shifts between a flow and no flow condition, while diastolic blood pressure is detected by sensing a characteristic change in slope of blood pulse wave form changes occurring with changing cuff pressures which occurs at a cuff pressure equal to the diastolic pressure. An approach for correcting the systolic and diastolic pressure measurements obtained by this method at one point of the body to give equivalents of the systolic and diastolic blood pressure at another point is also provided.

DETAILED DESCRIPTION OF THE DRAWINGS

FIG. 1 is a diagrammatic representation of the arrangement according to the present invention;

FIG. 2 is a block diagram representation of the analyzing circuitry shown in FIG. 1;

FIG. 3 is a plot of amplitude normalized characteristic pressure pulse wave forms for various occluding cuff pressures;

FIG. 4 is a diagrammatic representation of the pressure wave form index calculating circuitry referred to in FIG. 2.

DETAILED DESCRIPTION

Figure 5:
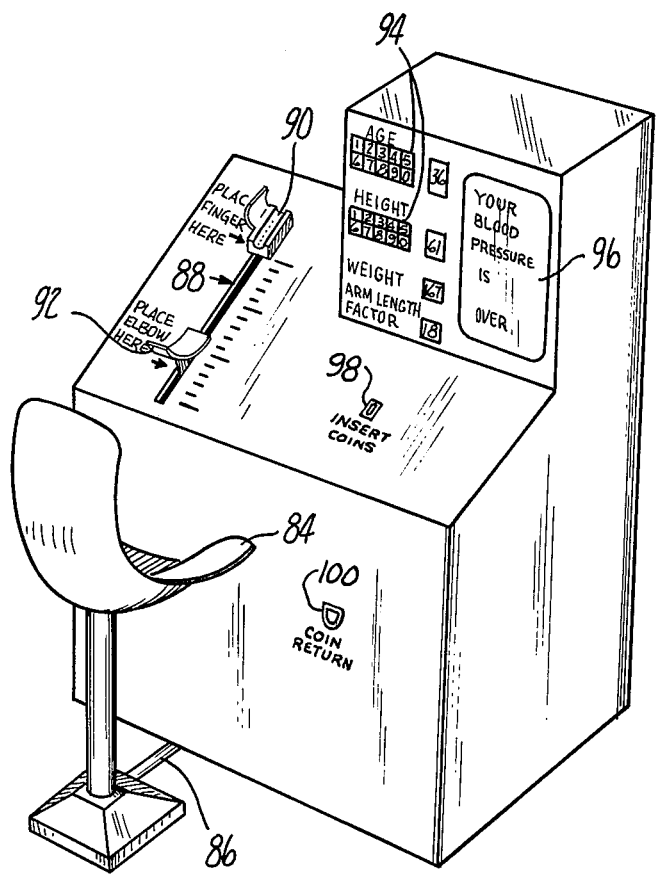
FIG. 5 is a perspective representation of a console and display for automated application of the arrangement depicted in FIG. 1.

In the following detailed description, certain specific terminology will be utilized and a particular embodiment described for the sake of clarity in accordance with the requirements of 35 USC 112, but it is to be understood that the practice of the invention is capable of assuming many forms within the scope of the invention.

Referring to the drawings, and particularly FIG. 1, the arrangement according to the present invention includes means for applying a pressure force to a body member taking the form of an inflatable cuff 10 which is adapted to encircle the body member such as the finger shown. The inflatable cuff 10 is provided with a pressurizing circuitry 12 so as to provide means for changing the pressure force applied between a pressure lever greater than that which will occlude the arterial flow in the encircled member to a pressure level within the cuff 10, less than the diastolic or the pressure level at which unoccluded blood flow will occur.

This pressurizing circuitry 12 includes a solenoid valve 14 and a needle valve 16, a pressure regulator and filter 18, a check valve 20, and an adjustable pressure switch 22, all in communication with a pneumatic pump 24 and a bypass relief 26. In operation the pneumatic pump 24 builds up to a relatively high pressure which causes the adjustable pressure switch 22 to open and pressurize the region in the circuit up to the solenoid valve 14 which is initially in a closed position. The bypass relief 26, in the meantime, opens at a slightly higher pressure causing the adjustable pressure switch 22 to close so that the region in the circuitry up to the solenoid valve 14 acts as an accumulator for pressurized air. The solenoid valve 14 is then activated to open and cause the pressurization of the inflatable cuff 10 via flow regulating needle valve 16 and pressure regulator and filter 18. Solenoid valve 14 is then closed and a second solenoid valve 28 opened which allows a controlled bleed down at a relatively constant rate through a calibrated orifice 30 adjusted to produce the proper rate of bleed.

The pressure conditions existing within inflatable cuff 10 during this period are monitored continuously by a pressure monitor 32 which generates corresponding electrical signals and transmits the same to analyzing circuitry 34.

The blood flow condition in the fingertip downstream of the cuff 10 is monitored by a flow monitor 36 which detects either a flow or no flow condition and transmits a signal indicative of this transition to analyzing circuitry 34. This flow monitor 36 may advantageously be of the type such as a plethysmograph, a well known device which utilizes either optical or impedance methods to determine the flow condition or non-flow condition in the fingertip. Inasmuch as this is a conventional device, a detailed description thereof is not here included.

Suffice it to say that a relative change in size of the finger is detected by either a change in opacity or electrical impedance as measured by the plethysmograph and a signal indicative thereof generated.

Since certain physiological data may also be useful for purposes of converting the blood pressure readings obtained at one point on the body such as the finger, to an equivalent pressure readings at another point such as the upper arm, a physiological data source 38 can also be included.

The analyzing circuitry 34 processes these signals and displays at 40 the results thereof, i.e. the systolic and diastolic pressure readings.

Referring to FIG. 2 the details of the analyzing circuitry 34 are represented in block diagram form. The signals from the pressure monitor 32 are transmitted to a pressure reading averager 42 which takes the pressure readings which vary slightly from the effects of the blood flow pulse and produces equivalent steady pressure readings which are sampled throughout the pressurization cycle at regular intervals by a sample and hold 44 which in turn transmits the sampled data to a memory and read-out circuit 46, to record the pressure reading values sampled.

At the point in the pressurization when the pressure in the inflatable cuff 10 declines to a level where flow begins in the fingertip, signal generated by the blood flow monitor 36 corresponding to this change in condition is detected by appropriate detector circuitry 56 and transmits a signal to the pressure memory and read-out circuit 46 which interrogates the same and determines the cuff pressure at which the blood flow began, which pressure would correspond to the systolic blood pressure.

The same pressure monitor signals are transmitted to a high pass filter 48 which produces signals corresponding to the cuff pressure variations produced by the effects of blood pressure pulses. Signals corresponding to these individual pressure pulse variations are then transmitted to a wave form analyzer 50 which analyzes the wave shape over the entire course of a blood pressure pulse and produces a quantitative indicator of the wave form shape, i.e., the a wave form index value signals, the value of which is then transmitted to a calculation circuit 52 receiving signals corresponding to successive values of the wave form index value and the corresponding cuff pressure signal values. These signals values are sucessively transmitted to slope change calculation circuitry 54 which after the diastolic pressure point has been passed, analyzes this data to detect a change in slope in the plot of the wave form index signal values produced by circuits 50 and 52 as a function of cuff occluding pressure.

Circuitry 50, 52, and 54 are provided essentially to detect the transition of cuff pressure through the diastolic pressure point. It has been discovered as will hereinafter be described in greater detail that the changes in the pressure pulse wave form index values produced by an incremental decrease in cuff pressure, approach zero at the diastolic pressure point. This can be partially explained by considering the effect of the inflatable cuff 10 in throttling the arterial blood flow. That is, changes in cuff pressure between cuff pressures corresponding to completely occluded and completely unoccluded flow in the member encircled, produce a corresponding throttling effect on blood flow for each incremental increase or decrease in the cuff pressure, this functional relationship being essentially linear. Upon decline of pressure within the cuff 10 to the point where the arteries involved are virtually unoccluded, further declines in cuff pressure produce no effect. Circuitry 50, 52 and 54 attempt to utilize this fact to accurately, but simply and reliably determine diastolic pressure by detection of that cuff pressure at which the change in slope occurs.

A signal is then generated which interrogates the pressure memory and read-out 46 to determine the cuff pressure which existed at that point in time to determine the diastolic pressure.

These pressure values are then transmitted to correction circuitry 58 which taken together with physiological data from the data source 38 calculates the systolic and diastolic pressures which are displayed at 60 and 62, respectively.

Referring to FIG. 3 the phenomenon discussed in connection with the diastolic pressure determination can be better understood by reference to the successive plots 64 of pressure pulse variations induced in the inflatable cuff 10 by the effect of the blood pulse, at various values of cuff pressure which have been noted along the X-axis of that plot. These plots 64 have been "normalized" to a unity amplitude to remove the effects of variations in amplitude on the wave form index values. No pulses appear until the occluding cuff pressure declines to a level corresponding to systolic pressure indicated at 170 (millimeters of Hg). Hence, the arterial blood vessel is completely occluded until this point. It can be seen that successive blood pulses become progressively wider or less sharp with decreasing occluding cuff pressures. At the diastolic point, that is where the cuff pressure declines to a point where substantially unoccluded blood flow can occur, shown, for example, as 65 mm of Hg, this change in slope with decreases in cuff pressure ceases, and successive pulses 66 and 68 at lower cuff pressures are of similar form.

This cessation of change in the pulse wave forms can be detected quite simply in a number of ways, one of which is depicted in diagrammatic form in FIG. 4. The signals from the blood pressure variations circuitry 48 are transmitted to a pulse detector 70 which begins a data sampling cycle by detecting the leading edge of a blood pressure pulse, and resetting an averager 72, maximum detector 74, and minimum detector 76. The averager 72 determines the average value of the amplitude of the wave form over the course of the pulse cycle and outputs a signal corresponding thereto. The maximum detector 74 detects the maximum value of the input for that cycle while the minimum detector 76 detects the minimum value of this signal during the course of the pulse cycle, both detectors generating output signals also corresponding to these values.

These signals are combined in adders 78 and 80 respectively. Adder 78 takes the average pressure value reading received from the averager 72 and subtracts therefrom the minimum pressure value signal received from minimum detector 76 while adder 80 subtracts the maximum from the minimum reading. Both adders 78 and 80 transmit their output signal to a divider 82 which generates an output signal corresponding to the ratio of these signals which is then transmitted to the processing circuitry described in FIG. 2. It has been found that this signal gives a good indication of the differences in wave form produced by successive incremental changes in the blood pressure pulse wave, the differences between which decline to zero when transitioning from the throttled to the unthrottled condition of arterial flow produced by the cuff pressure declining through the diastolic pressure level.

Other alternatives would include circuitry wherein the pulse average value minus the pulse minimum value divided by the difference between the pulse median value and the minimum value, which has been found to be a reliable indicator of the pulse wave form.

It can be seen that this is relatively simple circuitry which would be quite reliable and not subject to false triggering due to noisy environments which the Korotkoff noise analyzers have been subject to.

As noted, the blood pressure readings determined at one body location may be converted to equivalent pressure readings corresponding to readings at another point, i.e. a cuff placed at the finger may be converted to equivalent readings at the upper arm so as to enable comparison with clinical data based on the surveys of the results from conventional clinical procedures in which blood pressure has been traditionally been obtained at the upper arm location.

Referring to FIG. 5, a console displaying arrangement suitable for self administered blood pressure tests of the sort having a capability for obtaining physiological correction data as shown. This would include a seat 84 having a weight scale means transmitting via a cable 86 signals indicative of the subject's weight. Further physiological data could be provided by a slide wire arrangement 88, which the subject would operate by placing a finger in the cuff assembly 90 and an elbow in an elbow socket 92 has been adjusted to the corresponding distance of the individual's arm to produce an electrical signal varying as a function of the length of the subject's arm. At the same time, such data as age and height may be punched in with keys so that the display 96 may read out data based on equivalent upper arm readings and also diagnostic data related to the physiological data obtained thereby.

Figure 6:
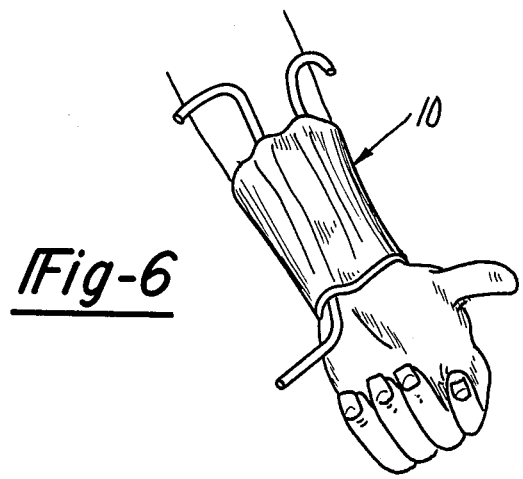
FIG. 6 is a perspective representation of the alternate application of the cuff to the wrist of a subject.

While FIG. 1 depicts an application of the inflatable cuff 10 to a finger, the approach according to the present invention also allows measurement of the wrist, which application is depicted in FIG. 6.

The arrangement according to the present invention is readily adapted to a coin operated machine and for this purpose the coin receiving slots 98 and coin return slot 100 may be included in the console as shown in FIG. 5, with appropriate internal controls such that the blood pressure measuring arrangement disclosed is activated upon the predetermined number of coins of a denomination being deposited therein.

It can be seen that this is a relatively simple system which is inherently quite reliable and is readily adapted to automated applications and as it does not rely on the Korotkoff sound analysis, can be applied to extremities such as the finger, wrist, etc. which would adapt this apparatus more readily to self-administered mass screening and for this reason it can be seen that the objects of the present invention have been obtained.

The embodiments of the invention in which an exclusive property or privilege is claimed are defined as follows:

1. A method of measuring blood pressure of a subject including the steps of:
   occluding blood flow in a body member by applying a pressure force to said body member, said application step including the step of changing said pressure force between a level whereat said blood flow is substantially occluded and a level whereat said blood flow is substantially unoccluded;
   monitoring said pressure applying said pressure force during said change in levels, including detecting variations in said pressures induced by blood pressure pulses;
   analyzing the shape of each wave form constituted by said pressure variations over the enitre course of each blood pressure pulse, including the step of calculating a wave form index value providing a quantitative indicator of the shape of said wave form;
   analyzing the changes in the wave form index values produced by successive changes in pressure applied in said occluding step;
   detecting a change in slope in the successive changes of said wave form index values at said pressure level corresponding to unoccluded blood flow;
   determining the average pressure monitored by said monitoring step at said pressure level, whereby the pressure level corresponding to diastolic blood pressure is measured.

2. The method of claim 1 further including the step of detecting a change in blood flow condition between a flow and a no-flow condition, and determining the average pressure monitored by said monitoring step at said change in blood flow condition whereby the pressure level corresponding to systolic is determined.

3. The method according to claim 1 wherein in said wave form shape analyzing step the average variation of said pressure variations is calculated and successive changes in said average are detected in said detecting step in order to determine said change in slope.

4. The method according to claim 1 wherein in said occluding step a finger is occluded by applying said pressure force.

5. A method according to claim 4 further including the step of developing physiological data of the subject and correcting said blood pressure determined to correspond to equivalent blood pressure reading at said subject's upper arm.

6. The method according to claim 1 wherein in said occluding step a wrist is occluded by applying said pressure force.

7. The method according to claim 1 wherein in said wave form analyzing step, said pressure variations wave forms are normalized whereby said index values are independent of pressure variation amplitude.

8. An arrangement for measuring blood pressure in a subject comprising:
- means for occluding blood flow in a body member, including means for applying a pressure force to said body member, said means further including means for changing said pressure force between a level wherein said blood flow is substantially occluded and a level wherein blood flow is substantially unoccluded;
- means for monitoring said pressure force, during said change in levels, including means for detecting variations in said pressures induced by blood pressure pulses;
- means analyzing the shape of each wave form constituted by said pressure variations over the entire course of each blood pressure pulse, said means including means producing a wave form index value signal providing a quantitative indicator value signal corresponding to the shape of said wave form;
- means analyzing the changes in wave form index signal values produced by successive changes in pressure applied by said occluding means;
- means for detecting a change in slope in the successive changes of said wave form index signal values at said pressure level corresponding to unoccluded blood flow;
- means for determining the average pressure monitored by said monitoring means at said pressure level, whereby said pressure level corresponding to diastolic pressure is measured.

9. The arrangement according to claim 8 further including means for detecting the changes in blood flow condition between a flow and a no-flow condition, further including means for determining the average pressure monitored by said monitoring means said change in blood flow condition whereby the pressure level corresponding to systolic is determined.

10. The arrangement according to claim 8 wherein said means for occluding blood flow in a body member includes an inflatable cuff adapted to encircle said body member and further includes means for pressurizing said inflatable cuff.

11. The arrangement as in claim 8 wherein said means analyzing the changes in wave form index signal values of said pressure variations includes means measuring the average pressure level variation during a said blood pressure pulse, and means for measuring successive changes in said average pressure level variation.

12. The arrangement according to claim 8 wherein said occluding means includes inflatable cuff adapted to encircle a finger of the subject and means for inflating said inflatable cuff.

13. The arrangement according to claim 12 further including means for generating physiological data corresponding to said subject and further including means for converting said blood pressure readings obtained from said finger location to an equivalent corresponding upper arm, blood pressure reading based on said physiological data.

14. The arrangement according to claim 8 wherein said occluding means includes inflatable cuff adapted to encircle a wrist of the subject and means for inflating said inflatable cuff.

15. The arrangement according to claim 8 further including coin receiving means and means activating said arrangement upon receipt of a predetermined number of coins of a proper denomination whereby said blood pressure measuring arrangement is coin operated.

16. The arrangement according to claim 8 wherein said means analyzing said pressure variation wave form shape includes means normalizing said pressure variation signal values whereby said index values are independent of pressure variation amplitude.

17. A method of measuring blood pressure of a subject including the steps of:
- occluding blood flow in a body member by applying a pressure force to said body member, said application step including the step of changing said pressure force between a level whereat said blood flow is substantially occluded and a level whereat said blood flow is substantially unoccluded;
- monitoring said pressure applying said pressure force during said change in levels, including detecting variations in said pressures induced by blood pressure pulses;
- analyzing each wave form constituted by said pressure variations over the entire course of each blood pressure pulse;
- analyzing the changes in the wave form of said pressure variations produced by successive changes in pressure applied in said occluding step;
- detecting a change in the successive changes of said wave form at said pressure level corresponding to unoccluded blood flow;
- determining the average pressure monitored by said monitoring step at said pressure level, whereby the pressure level corresponding to diastolic blood pressure is measured.

18. An arrangement for measuring blood pressure in a subject comprising:
- means for occluding blood flow in a body member, including means for applying a pressure force to said body member, said means further including means for changing said pressure force between a level wherein said blood flow is substantially occluded and a level wherein blood flow is substantially unoccluded;
- means for monitoring said pressure force, during said change in levels, including means for detecting variations in said pressures induced by blood pressure pulses;
- means analyzing each wave form constituted by said pressure variations over the entire course of each blood pressure pulse;
- means analyzing the changes in wave form of said pressure variations produced by successive changed in pressure applied by said occluding means;
- means for detecting a change in the successive changes of said wave form at said pressure level corresponding to unoccluded blood flow;
- means for determining the average pressure monitored by said monitoring means at said pressure level, whereby said pressure level corresponding to diastolic pressure is measured.

* * * * *

UNITED STATES PATENT OFFICE
CERTIFICATE OF CORRECTION

Patent No. 4,105,021        Dated August 8, 1978

Inventor(s)   William J. Williams et al.

It is certified that error appears in the above-identified patent and that said Letters Patent are hereby corrected as shown below:

Assignee should read -- Joseph H. Allen and Lawrence S. Weisman, Southfield and Madison Heights, Mich. --

Column 2, line 27, "enitre" should read -- entire --.

Signed and Sealed this

Twenty-seventh Day of March 1979

[SEAL]

Attest:

RUTH C. MASON  
Attesting Officer

DONALD W. BANNER  
Commissioner of Patents and Trademarks